United States Patent [19]
Sugawara

[11] Patent Number: 5,369,492
[45] Date of Patent: Nov. 29, 1994

[54] BONDING WIRE INSPECTION APPARATUS

[75] Inventor: Kenji Sugawara, Tokyo, Japan

[73] Assignee: Kabushiki Kaisha Shinkawa, Tokyo, Japan

[21] Appl. No.: 968,299

[22] Filed: Oct. 29, 1992

[30] Foreign Application Priority Data

Oct. 29, 1991 [JP] Japan ................................ 3-308358

[51] Int. Cl.⁵ ............................................ G01B 11/00
[52] U.S. Cl. .................................. 356/394; 356/237; 348/126
[58] Field of Search ................ 356/394, 237; 348/126

[56] References Cited
U.S. PATENT DOCUMENTS 5,030,008 7/1991 Scott et al. ........................... 356/394

FOREIGN PATENT DOCUMENTS 3-76137 4/1991 Japan .

*Primary Examiner*—F. L. Evans
*Attorney, Agent, or Firm*—Koda and Androlia

[57] ABSTRACT

An apparatus for inspecting conditions of bonding between, for example, a semiconductor chip and a lead frame including a camera that images objects such as bonding wires, and ball parts and crescents of the wires, a vertical illuminating assembly installed beneath the camera so as to illuminate the objects vertically, and a ring-form illuminating assembly made up of LED's arranged in a concentric circles so as to illuminates the objects from above diagonally. With such illuminating assemblies, clear images of the object are taken easily by the camera for inspection and measuring purposes.

2 Claims, 5 Drawing Sheets

BONDING WIRE INSPECTION APPARATUS

BACKGROUND OF THE INVENTION

1. Field of the Invention

The present invention relates to an apparatus for inspecting wires bonded between pads on a semiconductor chip and leads of a lead frame and more particularly to an illuminating device used in such an inspecting apparatus.

2. Prior Art

Japanese Patent Application Laid-Open ("Kokai") No. 3-76137 discloses one example of inspection apparatuses for bonding wires. This device inspects such wires as shown in FIGS. 5 and 6 which are bonded between pads 2 on a semiconductor chip 1 and leads 4 of a lead frame 3.

The inspection apparatus comprises as shown in FIG. 9: an inspection stand 10 for a sample 6 which has been bonded as shown in FIGS. 5 and 6; a multiple number of light bulbs 11 which illuminate the sample 6; a CCD camera 12 which images the wires 5 illuminated by the light bulbs 11 and outputs image signals; an image processing arithmetic unit 13 that processes the image signals from the CCD camera 12, recognizes the wire shapes and locates the bonding positions of the wires 5; and an X-Y table 14 that moves the CCD camera 12 around.

In this apparatus, the sample 6 is illuminated by the light bulbs 11, and the X-Y table 14 is driven so that the CCD camera 12 is positioned above the sample 6. Then, via the image processing arithmetic unit 13, the image signals of the sample 6 obtained by the CCD camera 12 are subjected to an enhancement (restoration) which includes noise elimination, emphasis of the edge area of the sample, and enlargement or reduction of the image, etc., so that the image of the sample can be seen clearly. Afterward, inspection and measurement are performed.

In the prior art apparatus as described above., however, there are limits on enhancement (restoration) of the image signals, which result in that the enhanced (restored) image differs greatly from the actual sample. In addition, the enhancement (restoration) operation usually takes time, and it is difficult to obtain reliable inspection and measurement results.

More specifically, as shown in FIGS. 5 and 6, the semiconductor chip 1 is bonded to the lead frame 3 via a paste 7 which is, for example, an epoxy resin, and the paste 7 is often squeezed out around the edges of the semiconductor chip 1. The squeezed out paste causes problems. When, for example, an inspection and measurement is made on the wire 5A by illuminating the wire 5A with the light bulbs 11, illumination from the direction A in FIG. 6 causes light, that is irregularly reflected by the paste 7, to enter the CCD camera 12. In this case, the brightness of the surface of the wire 5A and the brightness of the light that is irregularly reflected by the paste 7 are about the same; as a result, the CCD camera 12 cannot obtain a clear image of the wire 5A itself over the paste 7. Accordingly, the obtained image looks as if there is no wire 5A.

Furthermore, as shown in FIGS. 7 and 8, bonding is performed in each case with a ball part 5a, which is at the end of the wire extending out of a capillary of a bonding machine, being flattened on the corresponding pad 2. However, in the conventional illumination method, the shape (or the edges) of the bonded ball part and the shape (or the edges) of the crescent 5b of the wire 5 bonded to the lead 4 are not emphasized in the obtained image.

SUMMARY OF THE INVENTION

Accordingly, the object of the present invention is to provide a bonding wire inspection apparatus which obtains sharp images of bonded wires, ball parts on a pad and crescents of a lead, with reliable inspection and measurement capabilities.

The object of the present invention is accomplished by a unique structure of an inspection apparatus which includes: a camera that images the object to be inspected (sample), a vertical illuminating means that is installed beneath the camera and vertically illuminates the object to be inspected, and a ring-form illuminating means which is installed beneath the vertical illuminating means, the ring form illuminating means consisting of a multiple number of LED's installed in the form of concentric rings or circles and inclined toward the center of the optical axis of the camera.

With the structure above:

a. When the ball parts are inspected, the ring-form illuminating means is switched off, and only the vertical illuminating means is switched on. The reason for using the vertical illuminating means only is as follows:

The illumination provided by the vertical illuminating means strikes the ball parts perpendicularly. In this case, the pads surrounding the ball parts generally consist of vacuum-evaporated aluminum and create considerable irregular reflection from the surfaces. On the other hand, the surfaces of the ball parts are in an Au mirror surface state, and the shape of the ball parts shows little irregular reflection. As a result, the ball parts appear darker than the surroundings, which means that the shapes of the ball parts can be sharply reproduced by the camera.

b. When the crescents are inspected, both the vertical illuminating means and the ring-form illuminating means are switched on. The reason for using the both vertical and ring-form illuminating means is as follows:

When the crescents are illuminated by perpendicular illumination from the vertical illuminating means, the crescents show less irregular reflection than the leads. Thus, the crescents can appear darker than the leads. However, since there are indentations and projections on the leads, the perpendicular illumination by the vertical illuminating means causes some irregularity in brightness of the leads. This irregularity can be eliminated by an illumination in the inclined direction from the ring-form illuminating means. However, the illumination, which is done by the ring-form illuminating means from the direction of the lead to which the crescent is bonded, brightens a part of the crescent. This results in that a correct shape of the crescent is not obtained. Accordingly, the LED's which illuminate the crescent from the direction of the lead to which the crescent is bonded are switched off, so that the crescent can be sharply imaged by the camera. Experiments show that for the crescent inspection, an angle of approximately 45 degrees is optimal as the angle of inclination of the LED's in the ring-form illuminating means.

c. When the wires are inspected, the vertical illuminating means is switched off, and the ring-form illuminating means is switched on. The reason for this is as follow:

If the vertical illuminating means is switched on, irregular reflection from the area around the wire, that is, the semiconductor chip, leads, paste, etc. will enter the camera to a greater extent than the reflection from the wire. As a result, the area around the wire becomes bright, and the wire does not show a bright image. The reason for this is that the wire surfaces are in an Au mirror surface state. By the way, there are various bright and dark spots around each wire; accordingly, it is necessary, in the wire inspection, to make the entire area surrounding each wire dark so that only the wire is bright and the inspection precision is increased. Experiments show that an illumination at an angle of incidence of approximately 10 degrees is ideal for obtaining a bright image of the wire alone. With such a small angle of incidence, the amount of irregularly reflected light from portions other than the wire can be extremely small. However, if the individual wires are illuminated by LED's installed in the low-angle ring-form illuminating means, a portion of each wire is obscured by the paste. Thus, the LED's located in the direction of the lead to which the wire being inspected is bonded are extinguished, which brings a sharp image of the wire.

DETAILED DESCRIPTION OF THE INVENTION

One embodiment of the present invention will be described below with reference to FIGS. 1 through 4. In this embodiment, elements which are the same as those shown in FIGS. 5 through 10 are referred to by the same symbols, and a detailed description of those elements is omitted.

Figure 1:
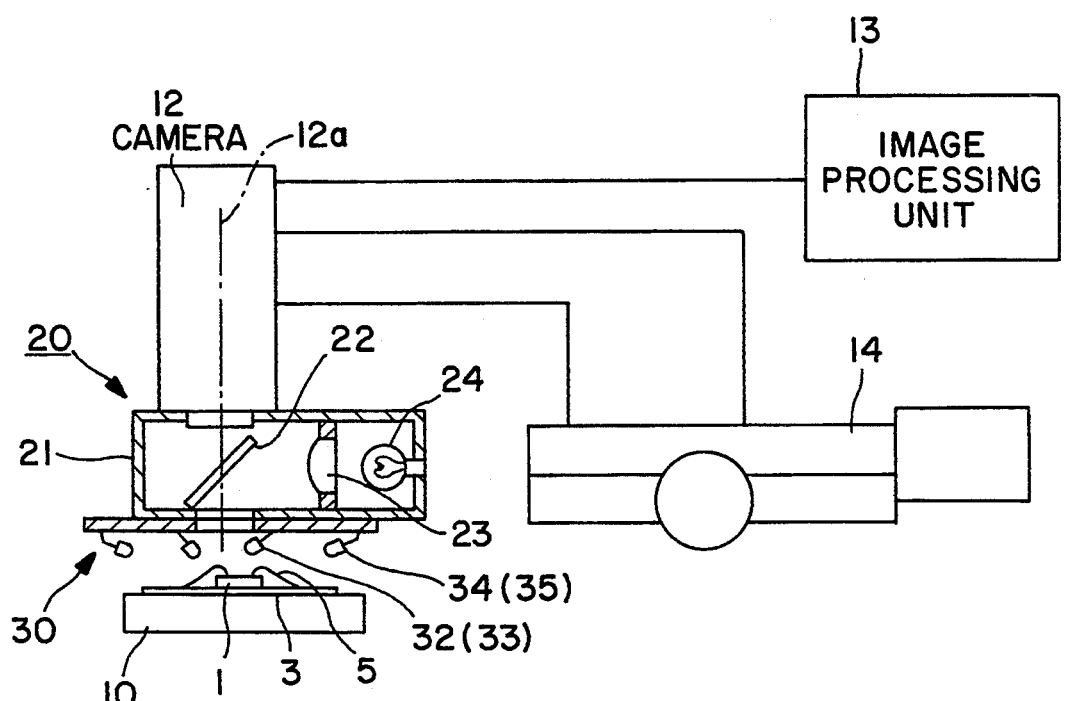
FIG. 1 is a schematic explanatory diagram which illustrates the structure of a bonding wire inspection apparatus according to the present invention.

As shown in FIG. 1, a vertical illumination assembly 20 is installed beneath a CCD camera 12. Inside the illumination box 21 of the vertical illumination assembly 20, a half-mirror 22 is installed so that it is positioned beneath the CCD camera A condenser lens 23 and a light bulb 24 are installed at one inner end of the vertical illumination assembly 20.

A ring-form illumination assembly 30 is installed beneath the vertical illumination assembly 20.

Figure 2:
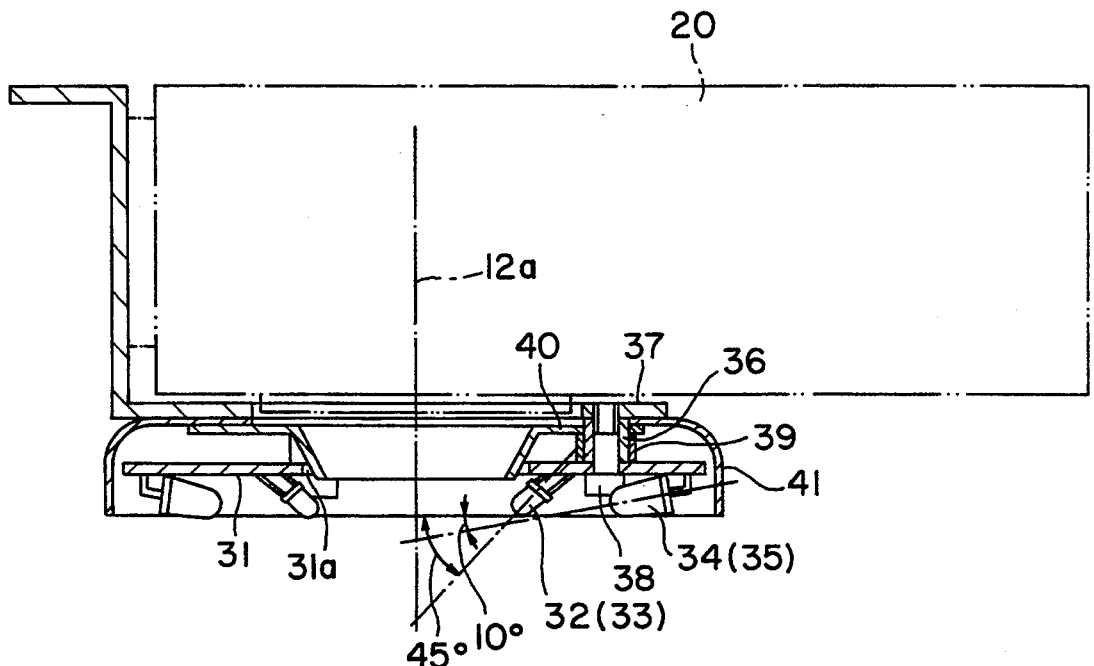
FIG. 2 is a cross section of the ring-form illuminating means used in the inspection apparatus in FIG. 1.
Figure 3:
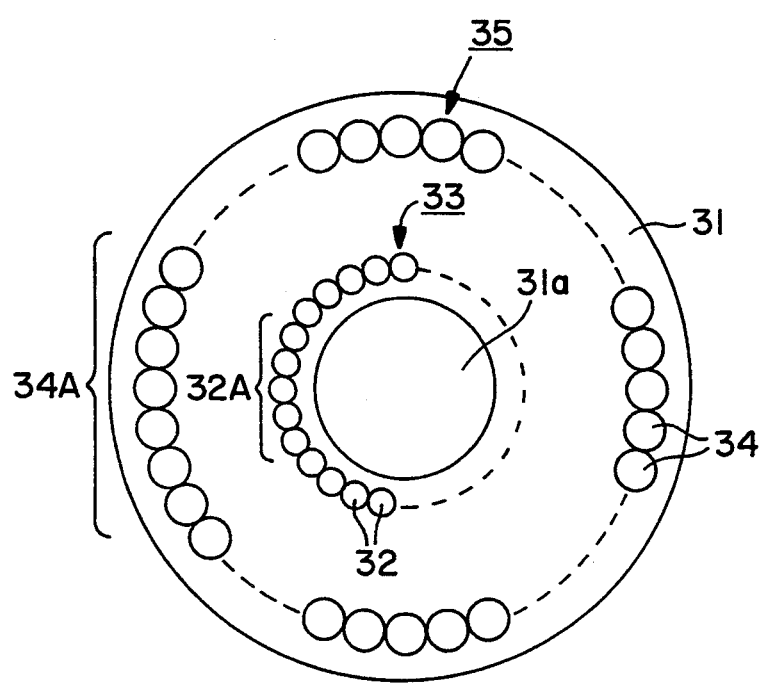
FIG. 3 is an explanatory diagram which illustrates the arrangement LED's of the ring-form illuminating means of FIG. 2.

The detail of the ring-form illumination assembly 30 is shown in FIGS. 2 and 3, and it comprises an inner ring-form illuminating device 33 that has a high angle of illumination and an outer ring-form illuminating device 35 that has a low angle illumination.

The inner illuminating device 33 is made up of plural LED's 32 installed in the form of a ring or circle which are mounted to an illumination holding plate 31 around a center opening 31a that is formed at the center of the holding plate 31. The outer illuminating device 35 is also made up of a plurality of LED's 34 mounted to the illumination holding plate 31. The LED's 34 of the outer illuminating device 35 are arranged in the form of a ring or circle around the inner ring-form illuminating device 33.

The respective circular rows of LED's 32 and 34 face toward the optical center axis 12a of the CCD camera 12. The LED's 32 of the inner illuminating device 33 with a high angle of illumination are inclined at an angle of approximately 45 degrees relative to a horizontal level. The LED's 34 of the outer illuminating device 35 with a low angle of illumination are inclined at an angle of approximately 10 degrees relative to the horizontal level.

An attachment plate 37 is mounted on the illumination holding plate 31 via a supporting column 36, and the illumination holding plate 31 is fastened to the attachment plate 37 by a screw 38 which is inserted into the supporting column 36. A spacer 39 is fitted around the supporting column 36, and a light-screening plate 40 and cover 41 are installed between the spacer 39 and the attachment plate 37.

In FIG. 2, the LED's 32 and 34 are shown only in the right and left sides of the Figure; and in FIG. 3, some of the LED's 32 and 34 are omitted with those omitted LED's shown by broken lines.

Figure 4:
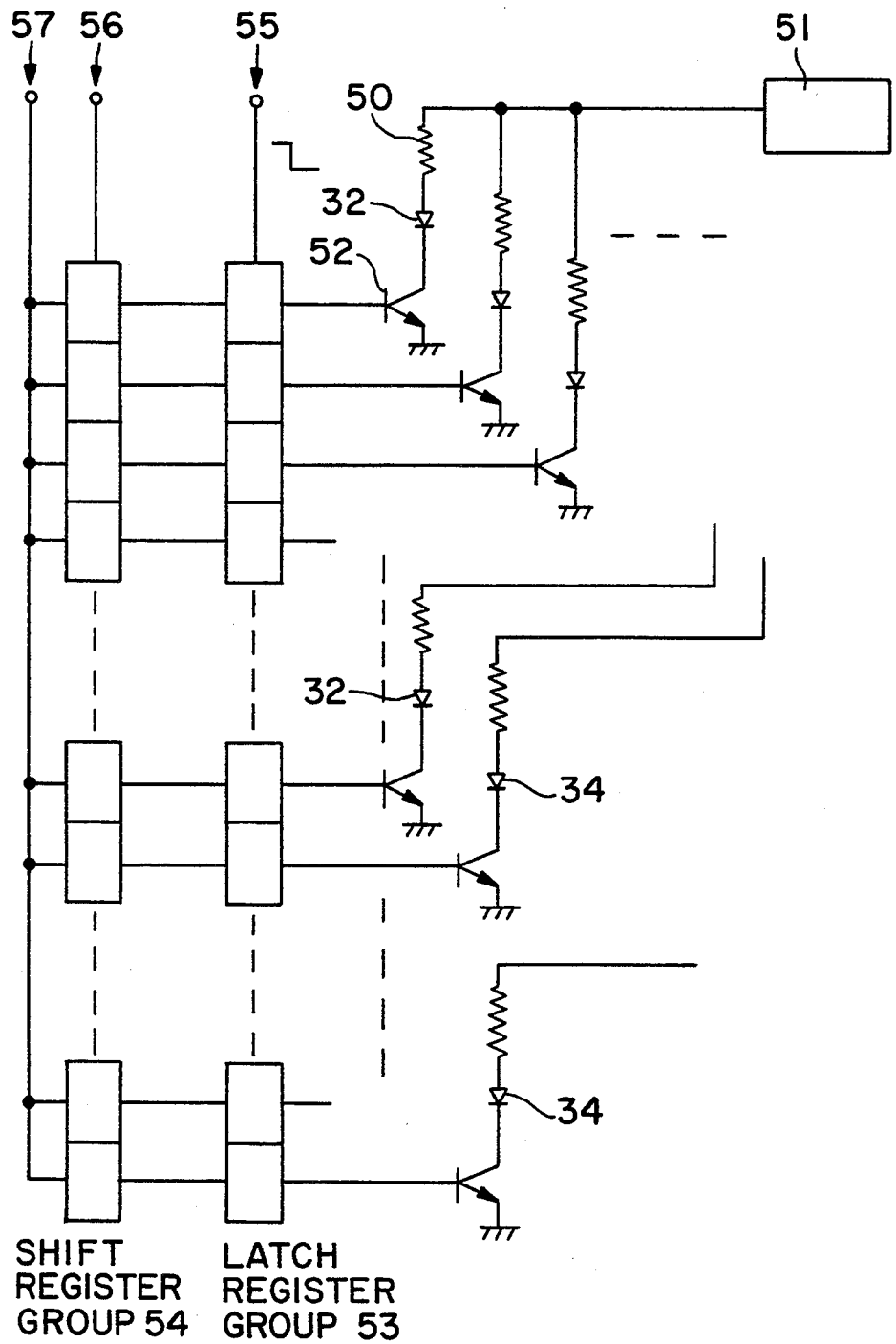
FIG. 4 is a block diagram of the illumination switching circuit used in the inspection apparatus.

The LED's 32 and 34 of the inner and outer ring-form illuminating devices 33 and 35 are operated by an illumination switching circuit that is shown in FIG. 4.

Figure 5:
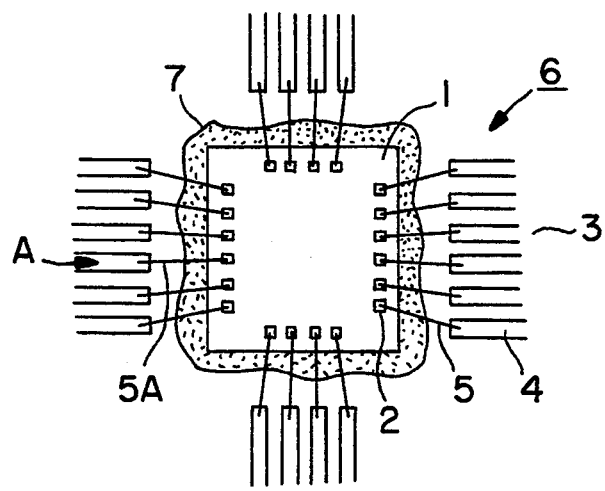
FIG. 5 is a plan view of a wire-bonded semiconductor device.

In FIG. 5, one end of each of the LED's 32 and 34 is connected to a programmable constant-voltage circuit 51 via a resistance 50, while the other end of each LED is connected to the collector of a transistor 52. The emitters of these transistors 52 are grounded, and the bases of the transistors 52 are connected to a shift register group 54 via a latching register group 53. A load signal 55 is inputted into the latching register group 53, a high-low (H-L) input signal 56 is inputted into the shift register group 54, and a clock signal 57 is inputted into each shift register of the shift register group 54.

The operation of the above-described embodiment will be given below.

Firstly, the inspection of the ball part 5a will be described.

In this case, the X-Y table 14 is driven, and the optical center axis 12a of the CCD camera 12 is brought so as to coincide with the position of the wire 5A. Then, the illumination of the ring-form illumination assembly 30 is switched off, and the vertical illumination assembly 20 is switched on.

The light from the light bulb 24 of the vertical illuminating assembly 20 passes through the condenser lens 23, reflected by the half-mirror 22 and then falls vertically on the ball part 5a. The pad 2 surrounding the ball part 5a generally consists of vacuum-evaporated aluminum and thus creates a considerable amount of irregular reflection from its surface; on the other hand, the surface of the ball part 5a is in an Au mirror surface state, and thus, also because of its shade, shows little irregular reflection. As a result, the ball part 5a appears darker than its surroundings, and the shape of the ball part 5a is sharply imaged by the CCD camera 12.

Secondly, the inspection of the crescent 5b will be described:

In this case, the X-Y table 14 is driven, thus bringing the optical center axis 12a of the CCD camera 12 to coincide with the position of the crescent 5b. Then, the vertical illumination assembly 20 and the inner ring-form illuminating device 33 of the ring-form illumination assembly 30 are switched on. But, the outer ring-form illuminating device 35 of the ring-form illumination assembly 30 is switched off.

The crescent 5b illuminated by perpendicular illumination from the light bulb 24 of the vertical illumination assembly 20 appears dark because the crescent 5b creates less irregular reflection than the corresponding lead 4. However, indentations and projections exist in the lead 4; as a result, the lead 4 shows some irregularity in brightness when it is perpendicularly illuminated by the vertical illumination assembly 20. Thus, the high-angle inner ring-form illuminating device 33 of the ring-form illumination assembly 30 is used to illuminate the crescent 5b from an angle of approximately 45 degrees. This illumination ensures that the irregularity in the brightness of the lead 4 caused by the perpendicular illumination is eliminated.

Figure 6:
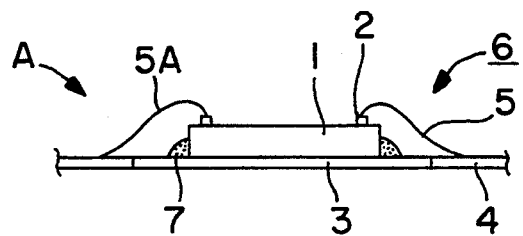
FIG. 6 is a front view thereof.
Figure 7:
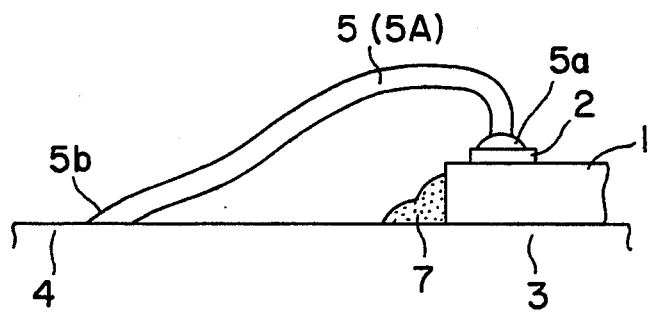
FIG. 7 is an enlarged front view of a bonding wire.
Figure 8:
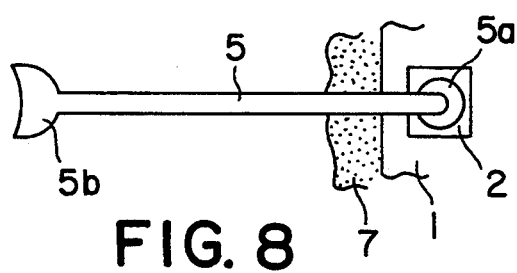
FIG. 8 is a plan view thereof.
Figure 9:
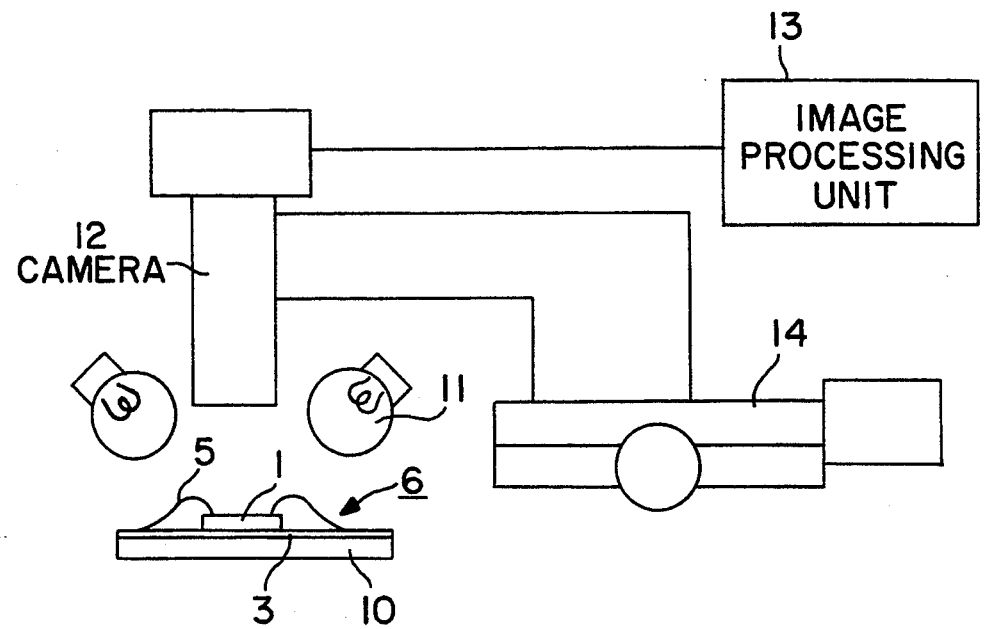
FIG. 9 shows a conventional bonding wire inspection apparatus.
Figure 10:
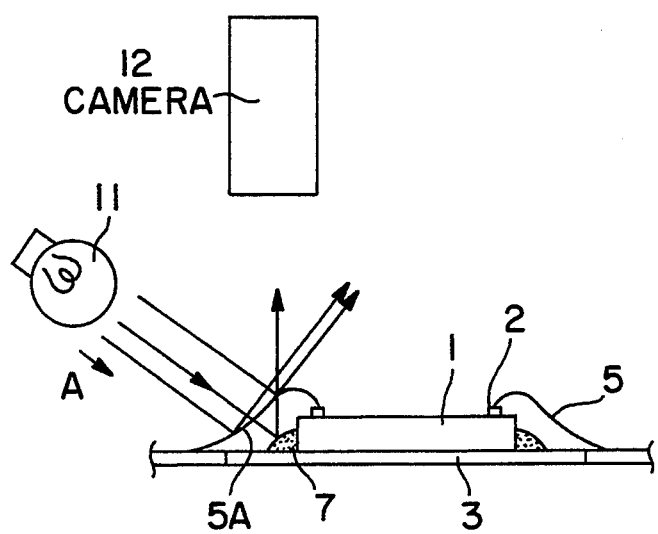
FIG. 10 is an explanatory diagram which illustrates a wire inspection method used in the conventional bonding wire inspection apparatus.

However, the illumination provided by the LED's of the inner illuminating device 33 from the direction indicated by arrow A in FIG. 6 (i. e., from the direction of the lead 4 to which the crescent to be inspected is bonded) brightens only a portion of the crescent 5b. Thus, a correct entire shape of the crescent 5b cannot be imaged.

In order to avoid this, the LED's 32 which illuminate the crescent 5b from the direction indicated by arrow A are switched off. In other words, the LED group 32A shown in FIG. 3 is switched off.

This is accomplished via the illumination switching circuit shown in FIG. 4 in the following manner: the respective shift registers of the shift register group 54 are successively switched by the clock signal 57; and in each case, a high (on) or low (off) input signal 56 is inputted; the high or low input signal 56 is successively stored in each register of the shift register group 54 via the clock signal 57; and then the signal stored in each register is transferred to the latch register group 53 via the load signal 55. As a result, only the LED's 32A which illuminate the crescent 5b from the direction indicated by arrow A are switched off. The LED's 32 to be switched off are designated beforehand by a program stored in a control circuit (not shown) in accordance with the object to be inspected.

With the above-described illumination method, the crescent 5b is sharply imaged by the CCD camera 12.

Thirdly, the inspection of the wires 5 will be described below:

In this case as well, the X-Y table 14 is driven so that the optical center axis 12a of the CCD camera 12 is made to coincide with the position of the wires 5A. Then, the vertical illumination assembly 20 and the high-angle inner ring-form illuminating device 33 of the ring-form illumination assembly 30 are switched off, and the low-angle outer ring-form illuminating device 35 of the ring-form illumination assembly 30 is switched on.

If the vertical illumination assembly 20 is switched on, reflected light from the area around the wire 5A (i.e., the semiconductor chip 1, lead 4 and paste 7) will enter the CCD camera 12 to a greater extent than reflected light from the wire 5A itself. Accordingly, the area surrounding the wire 5A becomes bright, and a bright image of the wire 5A cannot be obtained. The reason for this is that the surface of the wire is in an Au mirror surface state. There are various bright and dark spots around the periphery of each wire, and it is necessary in the wire inspection to make the entire area surrounding each wire dark (so that only the wire is bright) in order to increase the precision of inspection. Furthermore, since the angle of incidence of the LED's 32 of the inner ring-form illuminating device 33 is large, i. e., approximately 45 degrees, reflected light from sources other than the wire 5A will also be large when illuminated by the inner illuminating device 33.

Experiments shows that illumination at an angle of incidence of approximately 10 degrees is optimal for obtaining a bright image of the wire 5A only. By setting the angle of incidence to be as small as 10 degrees, the amount of light reflected directly by sources other than the wire 5A becomes extremely small.

However, if the wire 5A is illuminated by the LED's 34 of the outer ring-form illuminating device 35, a part of the wire 5A is obscured by the paste 7. Thus, the LED's 34A which illuminate the wire 5A from the direction indicated by arrow A in FIG. 6 (which is the direction of the lead 4 to which the wire 5A is bonded) are extinguished by an operation similar to that described in the case of the crescent inspection method, so that the wire 5A is imaged sharply by the CCD camera 12.

As described above, depending upon the object to be inspected and upon where the object to be inspected is on and/or between a chip and a lead frame, the vertical illumination assembly 20, the ring-form illuminating assembly 30, and/or a part of the LED's of the illuminating devices 33 and 35 of the ring-form assembly 30 are switched on and off so as to secure sharp images of the ball parts, crescents, wires, etc.

Furthermore, in the embodiment described above, the ring-form illumination assembly 30 is a double illuminating system consisting of the ring-form illuminating devices 33 and 35. However, it is possible to install such illuminating devices in three or four ranks. Moreover, when either the wires 5 or the crescents 5b are inspected and measured, only the high-angle illuminating device 33 or only the low-angle illuminating device 35 can be used.

As seen from the above, the inspection apparatus of the present invention comprises: a camera which images the object to be inspected, a vertical illumination assembly which is installed beneath the camera and illuminates the object to be inspected in a vertical direction, and a ring-form illumination assembly which is installed beneath the vertical illumination assembly and consists of a multiple number of LED's installed in the form of a ring and inclined toward the optical center axis of the camera. Accordingly, sharp images of bonded wires, ball parts on pads and crescents on leads are obtained; in other words, a reliable inspection and measurement operation of bonding is performed.

I claim:

1. A bonding wire inspection apparatus comprising:
  a camera which images an object to be inspected;
  a vertical illuminating means provided beneath said camera, said vertical illuminating means comprising a light source and a condenser lens so as to illuminate said object in a vertical direction;

a ring-form illuminating means provided beneath said vertical illuminating means, said ring-from illuminating means comprising plural LED's arranged in a form of a plurality of concentric coaxial circles with an angle of incidence of optical axes of LED's of inner circled LED's being larger than an angle of incidence of optical axes of LED's of outer circled LED's.

2. A bonding wire inspection apparatus according to claim 1, further comprising an illumination switching circuit by which a certain number of successive LED's of said circular LED's are turned off depending upon an object to be illuminated by said LED's.

* * * * *